United States Patent [19]

Cryz

[11] Patent Number: 4,755,381

[45] Date of Patent: Jul. 5, 1988

[54] KLEBSIELLA CAPSULAR POLYSACCHARIDE VACCINE

[75] Inventor: Stanley J. Cryz, Bolligen, Switzerland

[73] Assignee: Swiss Serum and Vaccine Institute Berne, Berne, Switzerland

[21] Appl. No.: 844,973

[22] Filed: Mar. 27, 1986

[51] Int. Cl.⁴ .................. C08B 37/00; A61K 31/715; A61K 39/108

[52] U.S. Cl. .................. 424/92; 435/852; 536/1.1; 536/123; 536/127; 536/128

[58] Field of Search .................. 424/92; 536/1.1, 127, 536/128, 123; 435/852

[56] References Cited

U.S. PATENT DOCUMENTS 4,663,160  5/1987  Tsay et al. .................. 424/92 X
4,711,779  12/1987  Porro et al. .................. 424/92

OTHER PUBLICATIONS

J. Biol. Chem. 256, 14, 1981, 7305–7310, Seid et al.
Infect. Imm. 24: 476–482 (1979), Riottot et al.
Infect. Immun. 31:71–77 (1981), Riottot et al.
Infect-Immun. 32:420–426 (1981) Fournier et al.
Infect. Immun. 45:139–142 (1984), Cryz, Jr. et al.
Infect. Immun. 50:225–230 (Oct. 1985), Crys. Jr. et al.
Kreger et al,—Gram-Negative Bacteremia—Mar., 1980, pp. 322–355.
Robert et al.—Infect Immun. 54:365–370, 1986.

*Primary Examiner*—Howard E. Schain
*Attorney, Agent, or Firm*—Bradford E. Kile

[57] ABSTRACT

The present invention relates to immunogenic preparations of Klebsiella species serotype-specific capsular polysaccharides. The invention involves the treatment of Klebsiella capsular polysaccharides in dilute sodium hydroxide to detoxify co-purified toxic lipopolysaccharides and to yield immunogenic vaccine preparations safe for parenteral administration to humans. The polyvalent vaccines prepared by use of the above vaccine are effective at providing protection against infections caused by Klebsiella species bacilli.

31 Claims, No Drawings

KLEBSIELLA CAPSULAR POLYSACCHARIDE VACCINE

BACKGROUND OF THE INVENTION

The present invention is directed to polyvalent immunizing preparations composed of nontoxic serotype-specific polysaccharide preparations. More particularly, the invention described herein relates to the treatment of purified capsular polysaccharides (CPS) derived from Klebsiella species bacilli, hereinafter referred to as Klebsiella, with a deacylating agent such as sodium hydroxide (NaOH) to yield a nonpyrogenic, immunogenic CPS preparation. The present invention also relates to the use of immunogenic Klebsiella species CPS to provide protection against Klebsiella infections. A vaccine formulated from such antigens can be utilized to actively immunize individuals at risk to Klebsiella infections.

The frequency of infections due to gram-negative aerobic bacilli, such as Klebsiella, has increased dramatically over the preceding three decades, concomitant with the widespread use of broad spectrum antibiotics. Of these infections, those classified as pneumonia or bacteremia carry the highest attendant fatality ratios which average roughly 25% and are in the range of 10% to 50%. As described in McGowan, J. E., Barnes, M. W., Finland, M., "Bacteremia at Boston City Hospital: occurrence and mortality during 12 selected years (1935–1972), with special reference to hospital acquired cases," J. Infect. Dis. 132: 316–335, 1975; Bryan C. S., Reynolds, K. L., Brenner, E. R., "Analysis of 1,186 episodes of gram-negative bacteremia in non-university hospitals: the effects of antimicrobial therapy," Rev. Infect. Dis. 5: 629–638 1983; Graybill, J. R., Marshall, L. W., Charache, P., Wallace, C. K., Melvin, V. B., "Nosocomial pneumonia. A continuing major problem," Am. Rev. Resp. Dis. 108: 1130–1140, 1973; and Cross, A., Allen, J. R., Burke, J., Ducel, G., Harris, A., John, J., Johnson, D., Lew, M., MacMillan, B., Meers, P., Skalova, R., Wenzel, R., Tenney, J., "Nosocomial Infections due to *Pseudomonas aeruginosa*: review of recent trends," Rev. Infect. Dis. 5 (Suppl.): S837–S845, 1983, Klebsiella is a leading cause of such life-threatening infections, being the most frequently isolated gram-negative bacterium from the lower respiratory tract and the second most common cause of bacteremia. At present, there exists no effective immunological means for the control of Klebsiella infections.

Numerous bacterial species, among them Klebsiella, possess a well-defined capsule which surrounds the bacterial cell in a viscous layer. The capsule is composed of repeating units of monosaccharides which form a high molecular weight polymer. Such capsular polysaccharides (CPS) confer the K (or capsular) antigenic specificity upon their respective bacterial cells.

Studies such as described in Riottot, M. M., Fournier, J. M., Pillot, J., "Capsular serotype specificity of the protection conferred on mice by *Klebsiella pneumoniae* ribosomal preparations," Infect. Immun. 24: 476–482, 1979; Riottot, M. M., Fournier, J. M., Jouin, H., "Direct evidence for the involvement of capsular polysaccharide in the immunoprotective activity of *Klebsiella pneumoniae* ribosomal preparations," Infect. Immun. 31: 71–77, 1981; and Cooper, J., McA., Rawley, D., "Resistance to Klebsiella pneumoniae and the importance of two bacterial antigens," Austral. J. Expt. Biol. Med. Sci. 60: 629–641, 1982, have shown that an experimental ribosomal vaccine and an experimental killed whole-cell vaccine are capable of providing a degree of protection against Klebsiella infections in experimental animal models. Protection was found to correlate with the induction of a serotype-specific anti-CPS immune response. However, prior attempts to evoke a protective immune response in mice by vaccination with CPS have been heretofore unsuccessful, and this failure has been attributed to the poor immunogenicity of CPS in mice, as noted in J. M. Fournier, C. Jolivet-Reynaud, M. M. Riottot and H. Jouin, Infect. Immun. 32: 420–426, 1981.

It has now been discovered that immunogenic preparations of CPS can be obtained from the culture supernatant of Klebsiella cultivated in a medium designed to support capsule production. These CSP antigens can subsequently be purified to a high degree, and this highly purified product has been shown to be immunogenic and non-pyrogenic in animals, as described in Cryz, S. J., Jr., Fürer, E., Germanier, R., "Purification and vaccine potential of Klebsiella capsular polysaccharide," Infect. Immun. 50: 225–280, 1985; and Cryz, S. J., Jr., Fürer, E., Germanier, R., "Safety and Immunogenicity of *Klebsiella pneumoniae* K1 Capsular Polysaccharide Vaccine in Humans," The Journal of Infectious Diseases, Vol. 151, No. 4, April, 1985. Furthermore, as noted in Cryz, S. J., Jr., Fürer, E., Germanier, R., "Prevention of fatal experimental burn wound sepsis due to *Klebsiella pneumoniae* KP1-0 by immunization with homologous capsular polysaccharide," J. Infect. Dis. 150: 817–822, 1984 and Cryz, S. J., Jr., Fürer, E. Germanier, R., "Protection against fatal *Klebsiella pneumoniae* burn wound sepsis by passive transfer of anticapsular polysaccharide," Infect. Immun. 45: 139–142, 1984, anti-serotype-specific CPS has been shown to be highly effective at preventing fatal experimental Klebsiella infections.

SUMMARY OF THE INVENTION

In one embodiment, the present invention comprises a method of preparing a Klebsiella vaccine having the steps of: deriving relatively purified capsular polysaccharides from Klebsiella bacteria; treating said capsular polysaccharides with a deacetylating agent; and recovering a nonpyrogenic immunogenic Klebsiella vaccine.

In another embodiment, the present invention comprises a method of preparing a polyvalent Klebsiella vaccine having the steps of: deriving capsular polysaccharides from at least 2 different serotypes of Klebsiella bacteria; treating said capsular polysaccharides with a deacetylating agent; recovering a nonpyrogenic, immunogenic capsular polysaccharide of each respective serotype and combining at least a portion of each of these capsular polysaccharides to form a polyvalent immunogenic vaccine.

In yet another embodiment, the present invention comprises an immunogenic Klebsiella vaccine comprising capsular polysaccharide derivatives.

In still another embodiment, the present invention comprises a polyvalent immunogenic Klebsiella vaccine containing a mixture of capsular polysaccharides formed from at least two different serotypes of Klebsiella bacteria.

In a further embodiment the present invention comprises an immunogenic Klebsiella vaccine prepared by deriving relatively purified capsular polysaccharides from Klebsiella bacteria, treating said capsular polysaccharides with a deacetylating agent; and recovering a nonpyrogenic immunogenic vaccine.

In yet a further embodiment, the present invention comprises a polyvalent immunogenic vaccine prepared by deriving capsular polysaccharides from at least 2 different serotypes of Klebsiella bacteria; treating said capsular polysaccharides with a deacetylating agent; recovering a nonpyrogenic, immunogenic capsular polysaccharide of each serotype; and combining at least a portion of each of these capsular polysaccharides to form a polyvalent immunogenic vaccine.

DETAILED DESCRIPTION OF THE INVENTION

The present invention is directed to an immunizing preparation composed of purified Klebsiella serotype-specific capsular polysaccharides. This novel immunizing agent is prepared by combining appropriate serotypes of capsular polysaccharides (CPS) derived from the capsular serotyping of Klebsiella human blood isolates with a deacylating agent such as NaOH. These polyvalent vaccines are useful for active immunization against Klebsiella infections when administered by the parenteral, oral or nasopharyngeal route. These vaccines may also be administered by the parenteral route to increase the serum antibody levels to said CPS.

A safe and immunogenic polyvalent Klebsiella serotype-specific capsular polysaccharide vaccine has been produced by the novel method of treating purified Klebsiella capsular polysaccharides with a deacylating agent such as dilute sodium hydroxide. The capsular polysaccharides are obtained by cultivating strains of Klebsiella of known capsular serotype on a medium designed to promote such production. The capsular polysaccharides are purified by co-precipitation with detergent, ethanol precipitation, extraction with organic solvents, and ultracentrifugation. Purified capsular polysaccharides are then treated in dilute sodium hydroxide to detoxify co-purified toxic lipopolysaccharide. The resulting capsular polysaccharides possess a molecular weight greater than or equal to $1 \times 10^6$ daltons, are immunologically reactive with respect to corresponding native capsular polysaccharides, are nontoxic for mice and guinea pigs, and are relatively nonpyrogenic (e.g. $\leq 0.3°$ C. rise in body temperature) in rabbits at a dose greater than or equal to 5 ug/kg body weight.

The polyvalent Klebsiella capsular polysaccharide vaccine of the present invention is safe and immunogenic in humans. The vaccine induces the production of opsonic antibody which is protective against fatal experimental Klebsiella infections.

As noted previously, prior studies have shown that an experimental ribosomal vaccine and an experimental killed whole-cell vaccine are capable of providing protection against Klebsiella infections in experimental animal models and protection was found to correlate with the induction of a serotype-specific anti-CPS immune response. However, prior attemps to evoke a protective immune response in mice by vaccination with purified CPS have been, at least in some instances, unsuccessful.

As described in the Cryz et al publications noted previously, CPS has been isolated and purified from the supernatant of Klebsiella KP1-0 (serotype 1) cultures. CPS was co-precipitated from cell-free culture supernatant by the addition of a detergent such as Cetavalon. The CPS was separated from the detergent by dissolving the precipitate in 1M $CaCl_2$, and the CPS was then removed from the solution by the addition of ethanol to equal 80% (vol/vol). The CPS was thereafter dissolved in distilled water and extensively extracted with an equal volume of chloroform:butanol (5:1). The aqueous phase was collected, dialyzed against distilled water to remove traces of the organic solvents and then centrifuged at $100,000 \times g$ for 16 hours to remove the majority of lipopolysaccharide (LPS) present. The CPS-containing supernatant was collected, and the ethanol added to 80% (vol/vol) to precipitate CPS. CPS was dissolved in distilled water and lyophilized. CPS prepared in this manner was composed primarily of carbohydrate and possessed a molecular weight of greater than $1 \times 10^6$ as determined by gel-filtration chromatography. Antisera evoked in response to immunization of rabbits with purified CPS was found to protect mice against fatal K. pneumoniae KP1-0 sepsis. Similarly, mice which were actively immunized with purified KP1-0 CPS were protected against fatal K. pneumoniae KP1-0 sepsis.

K. pnuemoniae KP1-0 CPS was found to evoke a specific immune response when administered by the subcutaneous route to humans. However, immunization carried a high attendant rate of local reaction characterized by pain, swelling and redness due to low levels of LPS contaminating the CPS. By the present invention, the contaminating LPS is detoxified by deacylation through treatment of the lyophilized CPS in a 0.1M NaOH-95% (vol/vol) ethanol solution. This procedure markedly reduces the pyrogenicity of the CPS as determined by intravenous administration to rabbits. Furthermore, such NaOH-treated CPS was found to be equally immunogenic in humans with a much reduced incidence of local reactions upon injection. Human immunoglobulin G (IgG) elicited in response to immunization with CPS has been found to offer a high degree of protection against fatal K. pneumoniae infections when passively transferred to mice. It is to be understood that other deacylating agents such as potassium hydroxide, lithium hydroxide and ammonium hydroxide may also be suitable for use in the present invention.

These and other features of the present invention will become fully apparent when the following detailed description of a preferred embodiment of the invention is read in conjunction with the accompanying tables, wherein:

Table 1 shows the chemical composition of six individual Klebsiella capsular polysaccharides and a hexavalent vaccine produced from these polysaccharides in one embodiment of the present invention;

TABLE 1

| | Chemical composition of individual Klebsiella capsular polysaccharides | | | | |
|---|---|---|---|---|---|
| | Component[A] (% dry weight) | | | | |
| Preparation | Carbohydrate | Nucleic Acids | Protein | Residual Moisture | KDO[1] |
| K2 polysaccharide | 79.6 | 1.32 | 1.03 | 9.5 | 0.04 |
| K3 polysaccharide | 73.7 | 0.88 | 0.73 | 8.5 | 0.10 |
| K10 polysaccharide | 56.3 | 1.59 | 3.39 | 7.7 | 0.15 |
| K21 polysaccharide | 70.7 | 0.97 | 1.57 | 9.5 | 0.06 |
| K30 polysaccharide | 70.1 | 0.55 | 2.44 | 11.5 | 0.16 |
| K55 polysaccharide | 63.2 | 0.36 | 0.71 | 9.2 | 0.04 |

[1]KDO = 2-keto-3-deoxyoctonate. Assay specific for the presence of LPS.

Table 2 shows the effect of treating the above-mentioned capsular polysaccharides in sodium hydroxide on molecular weight and pyrogenicity;

TABLE 2

Effect of sodium-hydroxide treatment on the molecular weight and pyrogenicity of Klebsiella CPS

| Serotype of CPS | NaOH treatment | $K_d$[1] | $K_d \leq 0.5$ (%)[1] | MPD[2] (ug) |
|---|---|---|---|---|
| 2 | No | 0.04 | 99.4 | <0.1 |
|   | Yes | 0.03 | 99.2 | >10 |
| 3 | No | 0.04 | 98 | 0.5 |
|   | Yes | 0.05 | 98 | >10 |
| 10 | No | 0.03 | 98.3 | <0.1 |
|   | Yes | 0.09 | 99.2 | >10 |
| 21 | No | 0.10 | 98.3 | 0.5 |
|   | Yes | 0.05 | 99.2 | >10 |
| 30 | No | 0.05 | 99 | 1 |
|   | Yes | 0.02 | 100 | >50 |
| 55 | No | 0.1 | 99.7 | 1 |
|   | Yes | 0.06 | 99.2 | 50 |

[1] As determined by chromatography over Sepharose CL-4B as previously described in Wong, K. H., Barrera, O., Sutton, A., May, J., Hochstein, D. H., Robbins, J. D., Robbins, J. B., Parkman, P. D., Seligmann, E. B., Jr., "Standardization and control of meningococcal vaccines, group A and group C polysaccharides," J. Biol. Standardization 5: 197-215, 1977.
[2] MPD = minimal pyrogenic dose; which is defined as the smallest amount of antigen which, when administered intravenously to rabbits, will evoke an +0.3° C. increase in body temperature. Amount of antigen is expressed as ug/ml/kg of rabbit body weight.

Table 3 shows the anti-capsular polysaccharide immunoglobulin G antibody response following the parenteral administration of the vaccine to human volunteers;

TABLE 3

IgG response following vaccination with Klebsiella polyvalent vaccine

| 50 ug | IgG ELISA titer (arithmetic mean with range) | | | | | |
|---|---|---|---|---|---|---|
|  | K2 | K3 | K10 | K21 | K30 | K55 |
| Pre-immune[1] | 3.68 (<2-8) | 6.3 (<2-16) | 6.9 (<2-16) | 9 (<2-16) | 7.6 (<2-32) | 8 (<2-32) |
| Peak[2] | 68.7 (8-256) | 50.5 (<2-256) | 71.2 (16-256) | 44.9 (<2-128) | 104 (16-512) | 68.7 (8-256) |
| Fold-increase[3] | 18.6 | 8 | 10.3 | 5 | 13.6 | 8.6 |
| Nr 4-fold increase or greater in titer/total | 21/22 | 18/22 | 20/22 | 19/22 | 19/22 | 20/22 |

[1] At the time of immunization
[2] Highest titer observed following vaccination.
[3] Mean peak titer divided by the mean pre-immune titer.

Table 4 shows the protective capacity of the evoked anti-capsular polysaccharide IgG antibody response against fatal Klebsiella infections;

TABLE 4

Protective capacity of pre-immune and post-immune IgG against fatal Klebsiella K2 burn wound sepsis

| IgG-transferred[1] | Challenge strain[2] | Mortality rate[3] | p[4] |
|---|---|---|---|
| Pre-immune | Klebsiella 1614 | 70% | <0.01 |
| Post-immune |  | 0 |  |
| Pre-immune | Klebsiella 98 | 70% | <0.01 |
| Post-immune |  | 0 |  |
| Pre-immune | Klebsiella E32 | 100% | <0.05 |
| Post-immune |  | 50% |  |
| Pre-immune | Klebsiella B5055 | 90% | <0.05 |
| Post-immune |  | 30% |  |
| Pre-immune | Klebsiella 1737 | 60% | <0.01 |
| Post-immune |  | 0 |  |

[1] IgG (0.3 ml) was transferred intravenously 24 hrs prior to challenge. ELISA titers were less than 2 for pre-immune IgG (derived from sera prior to immunization) and 256 for post-immune IgG (derived from vaccinees 28 days post-immunization).
[2] All strains were capsular serotype 2. The challenge dose was approximately $5 \times 10^1$ bacteria.
[3] Groups of 10 mice were used.
[4] Chi-square analysis.

Table 5 shows the anti-capsular IgG antibody titer for an immune intravenous gammaglobulin prepared from the sera of donors immunized with the hexavalent vaccine as compared to a preparation produced from normal human serum;

TABLE 5

| IVIG preparation | IgG titers to Klebsiella CPS's present in hyperimmune and normal IVIG | | | | | |
|---|---|---|---|---|---|---|
|  | IgG ELISA Titer Capsular Serotype | | | | | |
|  | 2 | 3 | 10 | 21 | 30 | 55 |
| Globuman | 32 | 64 | 256 | 64 | 64 | 128 |
| Klebsiella immune-IVIG | 4096 | 4096 | 4096 | 4096 | 8192 | 8192 |

Table 6 shows the ability of the above-mentioned immune gammaglobulin to promote the phagocytosis and killing of Klebsiella test strains;

TABLE 6

Promotion of Phagocytosis and Killing of Klebsiella by IVIG Preparations

| IVIG 2 | Bacterial killing Bacterial strain (serotype) | | | | | |
|---|---|---|---|---|---|---|
|  | K. pneumoniae B 5505 (2) | K. ozaenae C 5046 (3) | K. pneumoniae 919 (10) | K. pneumoniae 1702 (21) | K. pneumoniae 7824 (30) | K. pneumonia 3985 (55) |
| None | 0 | 0 | 0 | 0 | 25 ± 5 | 0 |
| Klebsiella Immune-IVIG | 75 ± | 94 ± 1 | 95 ± 3 | 97 ± 0 | 99 ± 0 | 80 ± 1 |
| Globuman | 0 | 0 | 25 ± 0 | 80 ± 4 | 46 ± 1 | 24 ± 1 |

1 Expressed as percent of original bacterial inoculum ($1 \times 10^6$ C.F.U.) killed after incubation for 120 minutes in the presence of PMN's ($1 \times 10^6$) and NHS (10% for strains B 5505 and 5056 and 5% for remaining strains).
2 IVIG's used at a final concentration of 1%.

Table 7 shows a comparison between the protective weight (on a weight basis) of the immune gammaglobulin and a normal gammaglobulin (globuman) preparation against fatal Klebsiella infections.

TABLE 7

Protection against fatal Klebsiella burn wound sepsis afforded by IVIG preparations

| IVIG transferred | Dose (mg/kg) | Mortality Nr. dead/total (%) | Mean time to death (hr) | p[1] |
|---|---|---|---|---|
| Human Albumin | 500 | 13/15 (87%) | 103.4 | |
| Globuman | 500 | 5/16 (31%) | 124.8 | <0.01 |
| | 50 | 10/15 (67%) | 88.8 | NS |
| | 5 | 12/15 (80%) | 96 | NS |
| Klebsiella immune-IVIG | 500 | 1/16 (6%) | 144 | <0.01 |
| | 50 | 4/15 (27%) | 138 | <0.01 |
| | 5 | 5/15 (33%) | 115.2 | <0.01 |

[1]Significance refers to mortality as compared to the human albumin-treated control group. NS = not significant, p > 0.05. Calculated by chi-square analysis.

In the following examples, capsular polysaccharides were isolated and purified from the following strains of Klebsiella:

K. pneumoniae 5055: capsular serotype 2;
K. ozaenae C5046: capsular serotype 3;
K. pneumoniae 919: capsular serotype 10;
K. pneumoniae 1702-49: capsular serotype 21;
K. pneumoniae 7824: capsular serotype 30; and
K. pneumoniae 3985-51: capsular serotype 55.

The above strains were supplied to the Swiss Serum and Vaccine Institute on May 19, 1983 by I. Orskov, Statens Seruminstitut, Copenhagen, Denmark and are capsular serotype reference strains. All strains are stored lyophilized in ampules.

Preparation of Klebsiella cultures for purification of CPS proceeded as follows. An ampule containing a lyophilized culture is opened, reconstituted and inoculated onto agar plates. The plates are grown for 18-24 hours at 37 degrees C. A loopful of culture is then used to inoculate 30 ml of HYEM broth [2% (wt/vol) Hy-case-SF (Humko Sheffield, Memphis, Tenn., USA), 0.3% (wt/vol) yeast extract (Difco Laboratories, Detroit, Mich., USA)], and 2% (wt/vol) maltose added as a 10% sterile stock solution in a 125 ml flask. The culture was grown at 37 degrees C., 100 RPM, for 8 hours. One ml of this culture is used to inoculate 500 ml of HYEM broth in a 2 L baffled Erlenmeyer flask. These cultures (8 flasks for a total of 4 L of medium) are grown at 37 degrees C., with shaking (100 RPM) for 16 hours. At the termination of cultivation the microbial purity of each flask is confirmed by gram-stain. It is to be understood that by the present invention other growing conditions for Klebsiella and conditions for purifying CPS may be utilized, if desired, though not necessarily with equal results.

Bacterial cells are removed by two rounds of centrifugation at 8,000×g for 30 minutes in sterile plastic centrifuge bottles using a Sorval RC-2B centrifuge. The supernatant is sequentially filtered through a 0.80 um abd a 0.45 um millipore filter (Millipore Corp., Bedford, Mass., USA).

All subsequent work was performed using autoclaved glassware or plasticware. Cetavlon (N-cetyl-N,N,N-trimethyl-ammonium bromide, E. Merck and Co.), as a 10% (wt/vol) stock, was added to the cell-free culture supernatant to yield a final concentration of 0.5% (Wt/vol). The mixture was stirred for 30 minutes at room temperature and a precipitate formed. The resulting CPS-containing precipitate was collected by centrifugation at 5,000×g for 30 minutes. The supernatant was discarded and the precipitate resuspended in approximately 100 ml of 1M $CaCl_2$. The mixture was stirred at ambient room temperature until the precipitate was dissolved. Ethanol, technical grade, was added to equal a final concentration of 80% (vol/vol) to precipitate the CPS. The precipitate was collected by centrifugation at 5,000×g for 30 minutes and dissolved in roughly 100 ml of distilled water. The solution was extracted with an equal volume of chloroform-butanol (5:1) until there was no visible white precipitate at the interphase, which typically required 3-5 rounds of extraction. After each extraction the material was centrifuged at 1,000×g for 15 minutes to increase the sharpness of the interphase. The material at the interphase and the organic phase was discarded. The CPS-containing water phase was dialyzed against distilled water at 4 degrees C. and at a minimum of 2×50 volumes of water. The dialyzed material was then centrifuged at 100,000×g for 18 hours (Beckman Model L2-65B, ultracentrifuge) to pellet the lipopolysaccharide (LPS). The supernatant was collected and the CPS precipitated by adding ethanol to equal a final volume of 80% (vol/vol).

The precipitated CPS was collected by centrifugation at 5,000×g for 30 minutes and dissolved in 100 ml-150 ml of sterile distilled water. The CPS solution (15-20 ml) was dispensed into sterile glass flasks (50 ml total volume) of known weights, capped, frozen at −70° C. for a minimum of 4-5 hours and lyophilized. After lyophilization the bottles were again weighed, and the initial weight subtracted to yield the quantity of material contained within the bottle. This material (stored at 4° C.) was labeled as to content, lot number, amount (weight of CPS) and date of production.

Detoxification of the trace amounts of LPS present in preparations of CPS was accomplished by deacylation as follows. Each serotype (purified from each of the six strains designated in Table 1) of lyophilized CPS (17.5 mg) was placed in 20 ml of a 0.1N NaOH-95% ethanol solution contained in a sterile Erlenmeyer flask. The flasks were placed on a rotary shaker at 37° C. and shaken for 30 minutes at 75 RPM. The liquid was removed with a Pasteur pipette and 20 ml of sterile phosphate-buffered saline pH 7.4 added to the vessel. The solution was lowered to pH 7 by the dropwise addition of sterile 1% $CH_3COOH$. The CPS were allowed to dissolve overnight at 4° C. The CPS solutions (1.2 mg/ml) were combined in equal parts in a sterile mixing vessel. The solution was then passed through a 0.45 um filter (Nalge Co., Rochester, NY, USA) under aseptic conditions. One ml of the sterile solution was placed aseptically into a 3 ml vial, capped, frozen at −70° C. and lyophilized under sterile conditions. The vials were sealed under vacuum. Each vial (termined final product) contained 50 ug each of six serotypes of CPS as indicated in Table 1 for a total of 300 mg per vial, which was termed one human dose. It is to be understood that the time in which the CPS material is treated with NaOH may be varied from 15 minutes 60 minutes although not necessarily with equivalent results.

Analysis of the bulk CPS and final product was as described below.

Protein: Protein was determined by the method described in Lowry, O. H., Rosenbrough, N. J., Farr, A. L., and Randall, R. J., "Protein measurements with the folin phenol reagent," (1951) J. Biol. Chem. 193: 265–275 using bovine serum albumin (Sigma Chemical Co., St. Louis, MO, USA) as a standard.

Nucleic acids: Nucleic acid content was quantitated by measuring the absorbance of 1 mg/ml CPS solution in distilled water at 260 nm in a 1 cm cuvette. The conversion rate is as follows: 1 optical density unit equals 50 ug of nucleic acid per ml.

Carbohydrate: Total carbohydrate content was measured by the phenol-sulfuric acid method using Dextran T-500 (Pharmacia Fine Chemicals, Uppsala, Sweden) as a standard.

Residual Moisture: Residual moisture was determined by use of a Type 26-321a moisture analyzer (Dupont Instruments, Monrovia, CA, USA).

Molecular Weight Determination: The molecular weight of the CPSs was determined by chromatography over Sepharose CL-4B (Pharmacia Fine Chemicals, Uppsala, Sweden). A 94 cm×1.5 cm column was calibrated using Blue Dextra 2000 (Pharmacia Fine Chemicals, Uppsala, Sweden) to determine the void volumen and $C_{14}$-acetic acid to determine the total column volume. A 5 mg sample of CPS was applied in 2 ml of phosphate-buffered saline (PBS), pH 7.4. The column was eluted with PBS and fractions (2.5 ml) were analyzed for carbohydrate content by the phenol-sulfuric acid mthod. The distribution constant (Kd) for the vaccine was calculated as described in Wong, K. H., Barrera, O., Sutton, A., May, J., Hochstein, D. H., Robbins, J. P., Robbins, J. B., Parkman, P. D., Seligmann, E. B., "Standardization and control of meningococcal vaccines, group A and group C polysaccharides," J. Biol. Standardization 5: 197–215, 197.

KDO: 2-Keto-3-deoxyoctanate (KDO), a component of LPS, was quantitated as described in Osborn, M. J., "Studies on the gram-negative cell wall I. Evidence for the role of 2-keto-3-deoxyoctonate in the lipopolysaccharide of *Salmonella typhimurium*," Proc. Natl. Acad. Sci. USA 50: 499–506, 1963.

The chemical composition of six serotypes of CPSs is shown in Table 1. The CPS preparations were composed primarily of carbohydrate with trace quantities of protein, nucleic acid and LPS being present.

Each CPS preparation was individually treated with dilute NaOH. The CPS preparations were analyzed before and after NaOH-treatment as a molecular weight and pyrogenicity in rabbits upon intravenous administration. (Table 2) It is known that the immunogenicity of CPS is dependent upon their relatively large molecular weight and that the safety of CPS upon parenteral administration to humans is inversely related to the pyrogenicity in rabbits, as described in the Wong, et al reference noted above. Therefore, an ideal CPS preparation would possess a high molecular weight and be nonpyrogenic. All native Klebsiella CPSs were of high molecular weight ($K_d$ less than or equal to 0.1 on Sepharose CL-4B) with the majority of carbohydrate eluting before a $K_d = 0.5$ has been reached. NaOH treatment had a negligible effect on these characteristics. Native CPS possessed a minimal pyrogenic dose (MPD) of less than or equal to 0.1 ug/kg to 1.0 ug/kg for rabbits (Table 2). Following treatment with NaOH, the MPD increased to greater than 50 ug/kg for some serotypes and corresponded to a minimim 20-fold decreased in pyrogenicity for all of the serotypes tested. Therefore, treatment of Klebsiella CPS with NaOH results in large molecular weight antigenic fractions which are nonpyrogenic.

A hexavalent Klebsiella CPS vaccine was then formulated. This vaccine contained 50 ug of NaOH-treated CPS derived from the six Klebsiella strains listed in Table 1 (1 human dose is equal to 300 ug of total antigen). Characteristics of the vaccine are as follows:

(1) The vaccine was nontoxic for animals. No mortality was observed among mice or guinea pigs which received one human dose of vaccine by intraperitoneal route. Furthermore, normal weight gain curves were noted following vaccine administration.

(2) The vacine was nonpyrogenic for rabbits. The administration of 50 ug of vaccine/kg rabbit body weight evoked a fever response of less than $+0.3°$ C.

(3) The vaccine was of a high molecular weight. The Kd of the vaccine when chromatographed over a Sepharose CL-4B column was 0 (equal to the void volume of the column) and greater than 99% of the material eluted with a Kd of less than 0.5.

(4) The vaccine was composed primarily of carbohydrate (72.8%, dry weight) with trace levels of protein (1.64%), nucleic acids (0.94%) and KDO. Residual water content was 9.3%.

(5) The vaccine is obtained as a sterile, while lyophilized powder.

Safety and immunogenicity of hexavalent Klebsiella CPS vaccine in humans:

Volunteers consisted of healthy individuals of both sexes aged 22 years to 62 years. Just prior to use the vaccine was reconstituted in sterile distilled water. The vaccine (0.5 ml) was administered subcutaneously in the deltoid region. Reactions to vaccination, including fever, local pain, swelling, erythema, induration, headache and malaise, were recorded by volunteers for 5 days post-vaccination. Venous blood samples were obtained from each individual at the time of vaccination and at 14 days and 28 days post-vaccination. The sera were collected and stored at $-20°$ C.

Approximately 35% (8 of 22) of the subjects reported a slightly painful reaction lasting for 24 hours. Three volunteers noted a systemic reaction characterized by a feeling of malaise and slight headache. All symptoms spontaneously disappeared within 24–48 hours after appearing and did not in any way limit the normal activities of the vaccinees.

The immunoglobulin G (IgG) response to each of the six vaccine components as determined by an enzyme-linked immunosorbent assay (ELISA) is shown in Table 3. The vaccine was found to be highly immunogenic in humans with 82% (K3) to 95% (K2) of the vaccinees responding with a 4-fold or greater increase in titer. The mean increase in IgG titers following vaccination ranged from 5-fold (K21) to 18.6 fold (K2).

To confirm the protective capacity of the immune response elicited by the hexavalent Klebsiella CPS vaccine, the following experiments were performed. IgG was isolated from the sera of 10 volunteers who showed a 4-fold or greater increase in titer to K2 CPS after immunization. IgG was also obtained from these volunteers prior to immunization. Mice (20 g female, NMRI strain) each received 2.3 mg of IgG in 0.3 ml of saline via the tail vein. Approximately 24 hours later the mice were burned and challenged with various virulent Klebsiella serotype 2 strains as previously described. The results are shown in Table 4. Pre-immune IgG which possessed undetectable levels of specific anti-K2 capsular antibody as determined by ELISA assay (titer of less than 2) was ineffective at preventing fatal sepsis (mortality rates of 60% to 100%). Highly significant protection (p less than 0.05 to p less than 0.01) was provided against all five Klebsiella K2 challenge strains by immune-IgG which possessed high levels (titer=256) of anti-K2 CPS antibody. These results show that the IgG antibody response in humans elicited upon vaccination with Klebsiella CPS is capable of providing highly significant protection against Klebsiella infections. Furthermore, the protective response is not strain-specific, i.e. anti-capsular serotype 2 antibody afforded protection against all five capsular serotype-2-bearing challenge strains.

Summarizing the data from Tables 3 and 4, NaOH-treated Klebsiella CPS formulated into a hexavalent vaccine was found to be safe and immunogenic in human volunteers. Greater than 80% of the vaccinees responded with a significant (4-fold or greater increase) IgG antibody response to the individual vaccine components. Human IgG antibody evoked by immunization with the above vaccine when passively transferred to mice was capable of affording a highly significant degree of protection against fatal Klebsiella infections. In contrast, IgG antibody prepared from the same volunteers prior to immunization offered no protection against fatal Klebsiella infections.

Production of a Human Hyperimmune Anti-Klebsiella Globulin Using the Hexavalent Klebsiella Vaccine:

Volunteers were immunized with the hexavalent Klebsiella CPS vaccine described above. Approximately six weeks later venous blood (an average of 240 ml per person) was collected from 13 individuals who showed a four-fold or greater increase in IgG ELISA titer to all six vaccine components following immunization. A gammaglobulin for intravenous use (IVIG) was prepared from the crude pooled sera through ethanol fractionation, ion-exchange chromatography, ultrafiltration and diafiltration. The protein content was adjusted to 50 mg/ml and the preparation lyophilized in a stabilizer solution. This preparation is referred to as Klebsiella immune-IVIG. Globuman (Swiss Serum and Vaccine Institute, Berne, Switzerland), an IVIG preparation, was prepared in an identical manner with the exception that the starting crude human plasma pool was obtained from human donors not immunized with the hexavalent Klebsiella CPS vaccine (i.e. normal human serum).

The Klebsiella immune-IVIG possessed substantially higher IgG ELISA titers (16-fold to 128-fold) than Globuman. (Table 5). In addition, only the Klebsiella immune-IVIG was found capable of facilitating the opsonization and subsequent killing of all six serotypes of test strains whose capsular antigen was represented in the vaccine when tested in an in vitro system (Table 6). The induction of such "opsonic" IgG antibody is of critical importance to the protective capacity of an immune-IVIG since removal of Klebsiella in a disease state is believed due to antibody-dependent phagocytosis and killing.

The ability of Globuman and Klebsiella immune-IVIG to prevent fatal Klebsiella burn wound sepsis when used in a prophylactic manner was determined. Mice (18-20 g female, NMRI strain) each received graded doses of the IVIG preparations (5 mg/kg to 500 mg/kg) or human albumin at 500 mg/kg (Albuman, Swiss Serum and Vaccine Institute, Berne, Switzerland) intravenously in 0.2 ml. Approximately 24 hours later the mice were burned and infected with 60 *K. pneumoniae* capsular type 2 bacteria. The results are shown in Table 7. The mortality rate for the group of mice which received human albumin as a control was 87%. Globuman, which possessed an IgG ELISA titer of 32 to the K2 antigen (expressed by the Klebsiella challenge strain) afforded significant protection (p less than or equal to 0.01) only at the highest dose tested (500 mg/kg). In contrast, the Klebsiella immune-IVIG provided good protection at doses as low as 5 mg/kg (1/100th that of Globuman).

Summarizing the data from Tables 5 through 7, an IVIG prepared from the pooled sera of volunteers immunized with the hexavalent Klebsiella CPS vaccine (Klebsiella immune-IVIG) had substantially higher IgG titers to the six vaccine components as compared to an IVIG prepared from pooled normal human serum. Only the Klebsiella immune-IVIG promoted the phagocytosis and subsequent killing of all six test strains of Klebsiella. The protective capacity of the Klebsiella immune-IVIG was 100-fold greater (on a weight basis) as compared to an IVIG produced from normal human sera by identical methodology.

Next, a polyvalent vaccine comprising 24 Klebsiella serotypes was prepared. A total of 703 Klebsiella blood isolates from 13 clinical centers in Europe and North America were studied as to capsular serotype.

The study of capsular serotypes was carried out as described in Palfreyman, J. M., "Klebsiella Serotyping by Counter-Current Immuno-Electrophoresis", Journal of Hygiene, Volume 81 #2 pp. 219-25 October (1978). The overall frequency of appearance is shown in Table 8. From these serotypes, particularly effective polyvalent vaccines comprising Klebsiella serotypes were prepared in accordance with the following. It was recognized that vaccination with Klebsiella capsular polysaccharide of certain serotypes also promoted the production of antibodies to certain other serotypes. Thus, for example, vaccination with CPS of serotype 2 promotes the production of antibodies to serotypes 2, 69 and 1; vaccination with CPS of serotype 21 promotes the production of antibodies to serotypes 21 and 11; vaccination with CPS of serotype 3 promotes the production of antibodies to serotypes 3 and 68; vaccination with CPS of serotype 10 promotes the production of antibodies to serotypes 10 and 7; and vaccination with CPS of serotype 64 promotes the production of antibodies to serotypes 64 and 14. This cross reactivity of certain serotypes is not necessarily reciprocal. For example, vaccination with CPS of serotype 35 promotes the production of antibodies to serotypes 35 and 33 to a much greater extent than vaccination with CPS of serotype 33 promotes the production of antibodies to serotypes 33 and 35.

In addition, although, as shown in Table 8, serotypes 1 and 39 occur with relative frequency in an absolute sense, these serotypes have thus far been endemic to particular locations and not particularly suitable for a vaccine of general application; although a vaccine containing these serotypes could be beneficially utilized at the particular locations of occurrence of these serotypes. Also, although Klebsiella serotype 27 occurs with a degree of relative frequency, inclusion of CPS of this serotype may not be appropriate in all instances because of a possible link between the occurrence of Klebsiella serotype 27 and ankylosing spondylitis.

In developing an effective polyvalent vaccine for Klebsiella, it is important to include CPS of sufficiently varied serotypes to provide a reasonable degree of protection. Also important, however, is to limit the number of serotypes to that which can be justified. In this regard, it may not be desirable to include in a single vaccine CPS of every serotype presented in Table 8. In addition to being inefficient, and to some practitioners, unethical, a vaccine containing all serotypes would in many instances cause increased discomfort to the vaccinee and would potentially result in antigen overload and suppress an immune response that would have otherwise been evoked from a vaccine with fewer different serotypes.

Although numerous vaccines of various serotype combinations are possible by means of the present invention, the preferred polyvalent vaccines are those containing Klebsiella serotypes 2, 3, 5, 9, 10, 15, 16, 17, 18, 21, 22, 25, 28, 30, 35, 43, 52, 53, 55, 60, 61, 62, 63 and 64; those containing Klebsiella serotypes 2, 3, 5, 9, 10, 15, 16, 17, 18, 21, 22, 25, 28, 30, 35, 39, 43, 52, 53, 55, 60, 61, 62, 63 and 64; and those containing Klebsiella serotypes 2, 3, 5, 9, 10, 15, 16, 17, 18, 21, 22, 25, 27, 28, 30, 35, 43, 52, 53, 55, 60, 61, 62, 63 and 64.

TABLE 8
Frequency of Capsular Serotypes Among Klebsiella Bacteremic Isolates

| Ranking | Capsular Serotype | Nr. Isolates | Frequency (% of all strains) |
|---|---|---|---|
| 1 | 2 | 63 | 8.96 |
| 2 | 21 | 55 | 7.82 |
| 3 | 55 | 34 | 4.83 |
| 4 | 53 | 20 | 2.85 |
| 5 | 25, 68 | 18 | 2.56 |
| 6 | 22 | 17 | 2.42 |
| 7 | 3, 10, 16, 43, 61, 64 | 15 | 2.13 |
| 8 | 17, 33, 62 | 14 | 2.00 |
| 9 | 7, 9 | 13 | 1.85 |
| 10 | 18, 28, 30 | 12 | 1.70 |
| 11 | 1, 39 | 11 | 1.57 |
| 12 | 27, 52, 60, 63 | 10 | 1.42 |
| 13 | 15 | 9 | 1.28 |
| 14 | 5, 8, 38, 48, 54 | 8 | 1.13 |
| 15 | 20, 41, 46 | 7 | 1.00 |
| 16 | 26, 31, 35, 80 | 5 | 0.71 |
| 17 | 11, 12, 14 | 4 | 0.57 |
| 18 | 13, 36, 44, 51, 56, 57 | 3 | 0.43 |
| 19 | 23, 24, 34, 37, 45, 47, 49, 50, 58, 70, 71 | 2 | 0.29 |
| 20 | 4, 6, 29, 40, 42, 65, 69, 72, 74 | 1 | 0.15 |
| 21 | 19, 32, 59, 66, 67, 79, 81, 82 | 0 | 0 |
|  | Non-typable | 71 | 10.10 |

In the following example, serotypes of NaOH-treated capsular polysaccharides were combined as described above with regard to the hexavalent vaccine to produce a vaccine comprising CPS derivative of the following 24 serotypes: 2, 3, 5, 9, 10, 15, 16, 17, 18, 21, 22, 25, 27, 30, 35, 43, 52, 53, 55, 60, 61, 62, 63 and 64. The vaccine was lyophilized. One human dose contained 50 ug of each antigen for a total of 1200 ug. Five healthy adult volunteers each received 1 dose of vaccine in 0.5 ml subcutaneously. One volunteer experienced pain at the injection site which began 4 hours after immunization and lasted approximately 24 hours. Venous blood was collected 28 days post-vaccination and the serum analyzed by ELISA for IgG titer to the CPS vaccine components. The results are shown in Table 9.

TABLE 9
Immunoglobulin G (IgG) Response Following Vaccination With 24-Valent Klebsiella CPS Vaccine

| CPS serotype | Mean IgG ELISA titer | | Mean-fold Increase |
|---|---|---|---|
| | Post-immune[1] | Post-immune[2] | |
| 2 | 2 | 28 | 14 |
| 3 | 5 | 41 | 8 |
| 5 | 5 | 60 | 14 |
| 9 | 13 | 92 | 7 |
| 10 | 7 | 18 | 2.5 |
| 15 | 9 | 41 | 4.5 |
| 16 | 16 | 54 | 3.3 |
| 17 | 7 | 19 | 2.7 |
| 18 | 6 | 77 | 12 |
| 21 | 5 | 17 | 3.4 |
| 22 | 5 | 14 | 2.8 |
| 25 | 6 | 35 | 5.8 |
| 27 | 4 | 19 | 4.4 |
| 30 | 7 | 26 | 3.7 |
| 35 | 3 | 8 | 2.7 |
| 43 | 4 | 14 | 3.5 |
| 52 | 8 | 29 | 3.6 |
| 53 | 5 | 15 | 3 |
| 55 | 5 | 19 | 3.8 |
| 60 | 3 | 26 | 8.6 |
| 61 | 4 | 179 | 45 |
| 62 | 2.5 | 19 | 7.6 |
| 63 | 4 | 18 | 4.5 |
| 64 | 5 | 20 | 4 |

[1]At the time of immunization.
[2]28 days post-immunization.

In summary, all 24 serotypes of Klebsiella CPS contained in the vaccine were capable of eliting a specific IgG antibody response upon parenteral administration to humans.

While preferred embodiments of the invention have been described herein, it will be obvious to those skilled in the art that various changes and modifications, especially pertaining to vaccine formulation as relates to number of serotypes of capsular polysaccharides incorporated, may be made within departure from the scope of the present invention.

I claim:

1. A method of producing a Klebsiella vaccine comprising the steps of:
preparing an essentially pure capsular polysaccharide mixture from Klebsiella bacteria;
treating said capsular polysaccharides with a deacetylating agent; and
recovering a nonpyrogenic immunogenic vaccine consisting of said capsular polysaccharides.

2. A method of preparing a polyvalent Klebsiella vaccine comprising the steps of:
preparing an essentially pure capsular polysaccharide mixture from Klebsiella bacteria of at least two different serotypes;
treating said capsular polysaccharides with a deacetylating agent;
recovering said capsular polysaccharides; and
combining at least a portion of said capsular polysaccharides of each said serotype to form a nonpyrogenic immunogenic vaccine.

3. A polyvalent immunogenic Klebsiella vaccine comprising a mixture of capsular polysaccharides purified from at least two different serotypes of Klebsiella bacteria by treatment with a deacetylating agent.

4. An immunogenic Klebsiella vaccine prepared by the steps of:
preparing a mixture of essentially purified capsular polysaccharides from Klebsiella bacteria;

treating said capsular polysaccharide mixture with a deacetylating agent; and recovering a nonpyrogenic immunogenic vaccine consisting of said capsular polysacchrides.

5. A polyvalent immunogenic vaccine prepared by the steps of:

preparing capsular polysaccharides of at least two different serotypes of Klebsiella bacteria;

treating said capsular polysaccharides with a deacetylating agent;

recovering said polysaccharides; and combining at least a portion of said capsular polysaccharides from each of said serotypes to form a nonpyrogenic immunogenic vaccine.

6. The method of claims 1 or 2 wherein said deacetylating agent comprises sodium hydroxide.

7. The method of claims 1 or 2 wherein said deacetylating agent comprises potassium hydroxide, lithium hydroxide or ammonium hydroxide.

8. The method of claims 1 or 2 wherein capsular polysaccharides are purified from a culture supernatent of Klebsiella cultivated in a medium comprising Hycase-SF, yeast extract and maltose.

9. The method of claim 2 wherein said capsular polysaccharides are purified from Klebsiella bacteria of serotypes 2, 3, 10, 21, 30, 55.

10. The method of claim 2 wherein said capsular polysaccharides are purified from Klebsiella bacteria of serotypes 2 and 21.

11. The method of claim 2 wherein said capsular polysaccharides are purified from Klebsiella bacteria of serotypes 2, 21 55.

12. The method of claim 2 wherein said capsular polysaccharides are purified from Klebsiella bacteria of serotypes 2, 21, 53, 55.

13. The method of claim 2 wherein said capsular polysaccharides are purified from Klebsiella bacteria of serotypes 2, 21, 25, 53, 55, 68.

14. The method of claim 2 wherein said capsular polysaccharides are purified from Klebsiella bacteria of serotypes 2, 21, 22, 25, 53, 55, 68.

15. The method of claim 2 wherein said capsular polysaccharides are purified from Klebsiella bacteria of serotypes 2, 3, 10, 16, 21, 22, 25, 43, 53, 55, 61, 64, 68.

16. The method of claim 2 wherein said capsular polysaccharides are purified from Klebsiella bacteria of serotypes 2, 3, 10, 16, 17, 21, 22, 25, 33, 43, 53, 55, 61, 62, 64, 68.

17. The method of claim 2 wherein said capsular polysaccharides are purified from Klebsiella bacteria of serotypes 2, 3, 7, 9, 10, 16, 17, 21, 22, 25, 33, 43, 53, 55, 61, 62, 64, 68.

18. The method of claim 2 wherein said capsular polysaccharides are purified from Klebsiella bacteria of serotypes 2, 3, 7, 9, 10, 16, 17, 18, 21, 22, 25, 28, 30, 33, 43, 53, 55, 61, 62, 64, 68.

19. The method of claim 2 wherein said capsular polysaccharides are purified from Klebsiella bacteria of serotypes 1, 2, 3, 7, 9, 10, 16, 17, 18, 21, 22, 25, 28, 30, 33, 39, 43, 53, 55, 61, 62, 64, 68.

20. The method of claim 2 wherein said capsular polysaccharides are purified from Klebsiella bacteria of serotypes 1, 2, 3, 7, 9, 10, 16, 17, 18, 21, 22, 25, 27, 28, 30, 33, 39, 43, 52, 53, 55, 60, 61, 62, 63, 64, 68.

21. The method of claim 2 wherein said capsular polysaccharides are purified from Klebsiella bacteria of serotypes 1, 2, 3, 7, 9, 10, 15, 16, 17, 18, 21, 22, 25, 27, 28, 30, 33, 39, 43, 52, 53, 55, 60, 61, 62, 63, 64, 68.

22. The method of claim 2 wherein said capsular polysaccharides purified from Klebsiella bacteria of serotypes 2, 3, 5, 9, 10, 15, 16, 17, 18, 21, 22, 25, 28, 30, 35, 43, 52, 53, 55, 60, 61, 62, 63 and 64.

23. The method of claim 2 wherein said capsular polysaccharides purified from Klebsiella bacteria of serotypes 2, 3, 5, 9, 10, 15, 16, 17, 18, 21, 22, 25, 28, 30, 35, 39, 43, 52, 53, 55, 60, 61, 62, 63 and 64.

24. The method of claim 2 wherein said capsular polysaccharides purified from Klebsiella bacteria of serotypes 2, 3, 5, 9, 10, 15, 16, 17, 18, 21, 22, 25, 27, 28, 30, 35, 39, 43, 52, 53, 55, 60, 61, 62, 63 and 64.

25. An immunogenic Klebsiella polyvalent vaccine comprising essentially pure capsular polysaccharides of serotypes 2, 3, 5, 9, 10, 15, 16, 17, 18, 21, 22, 25, 28, 30, 35, 43, 52, 53, 55, 60, 61, 62, 63 and 64.

26. An immunogenic Klebsiella polyvalent vaccine comprising essentially pure capsular polysaccharides of serotypes 2, 3, 5, 9, 10, 15, 16, 17, 18, 21, 22, 25, 28, 30, 35, 39, 43, 52, 53, 55, 60, 61, 62, 63 and 64.

27. An immunogenic Klebsiella polyvalent vaccine comprising essentially pure capsular polysaccharides of serotypes 2, 3, 5, 9, 10, 15, 16, 17, 18, 21, 22, 25, 27, 28, 30, 35, 43, 52, 53, 55, 60, 61, 62, 63 and 64.

28. The method of claim 22 wherein said vaccine further contains capsular polysaccharide of serotype 27.

29. An immunogenic Klebsiella vaccine comprising essentially pure capsular polysaccharides which have been treated with a deacetylating agent to render any contaminating lipopolysaccharides non-toxic.

30. The immunogenic Klebsiella vaccine of claims 29, 3, 4 or 5 wherein said capsular polysaccharide is purified from a culture supernatent of Klebsiella cultivated in a medium of 1 to 5% Hycase-SF, 0.1 to 1% yeast extract and 1–10% maltose.

31. The immunogenic Klebsiella vaccine of claims 29, 3 4 or 5 wherein said capsular polysaccharide derivatives have an average molecular weight of greater than $1 \times 10^6$ daltons.

* * * * *